(12) United States Patent
Fahrig et al.

(10) Patent No.: US 8,702,578 B2
(45) Date of Patent: Apr. 22, 2014

(54) POSITIONING DEVICE AND METHOD FOR POSITIONING A LOAD

(75) Inventors: Wolfram Fahrig, Forchheim-Kersbach (DE); Klaus Herrmann, Nürnberg (DE); Jochen Miguel Löseken, Bayreuth (DE)

(73) Assignee: Siemens Aktiengesellschaft, Munich (DE)

( * ) Notice: Subject to any disclaimer, the term of this patent is extended or adjusted under 35 U.S.C. 154(b) by 1048 days.

(21) Appl. No.: 12/130,826

(22) Filed: May 30, 2008

(65) Prior Publication Data

US 2008/0301872 A1 Dec. 11, 2008

(30) Foreign Application Priority Data

Jun. 5, 2007 (DE) .......................... 10 2007 026 114

(51) Int. Cl.
*A61G 10/00* (2006.01)
*A61G 7/00* (2006.01)
*G01B 7/00* (2006.01)

(52) U.S. Cl.
USPC ...................................... 600/1; 901/2; 901/23

(58) Field of Classification Search
USPC ........... 600/407, 1; 700/245; 702/150; 901/2, 901/23
See application file for complete search history.

(56) References Cited

U.S. PATENT DOCUMENTS

| | | | | |
|---|---|---|---|---|
| 4,475,160 A | * | 10/1984 | Inaba ....................... | 318/568.16 |
| 4,894,595 A | * | 1/1990 | Sogawa et al. ........... | 318/568.24 |
| 5,299,288 A | * | 3/1994 | Glassman et al. ........... | 700/245 |
| 2005/0234327 A1 | * | 10/2005 | Saracen et al. ................ | 600/407 |

FOREIGN PATENT DOCUMENTS

| | | |
|---|---|---|
| DE | 199 18 140 A1 | 10/2000 |
| DE | 103 12 025 A1 | 10/2004 |
| DE | 10 2004 013 174 A1 | 10/2005 |

OTHER PUBLICATIONS

German Office Action dated Mar. 17, 2008 with English translation.

* cited by examiner

*Primary Examiner* — Christine Hopkins
*Assistant Examiner* — Joshua D Lannu
(74) *Attorney, Agent, or Firm* — Lempia Summerfield Katz LLC

(57) ABSTRACT

A positioning device for positioning a load is provided. The positioning device includes a motor, a measuring device, and an evaluation device. The measuring device is associated with the motor, and is operable to ascertain measurement data that characterizes the motor current consumption by the motor in the positioning of the load. The evaluation device evaluates the measurement data that have been ascertained by the measuring device, so that in that way the loading of the positioning device by the load can be ascertained.

20 Claims, 3 Drawing Sheets

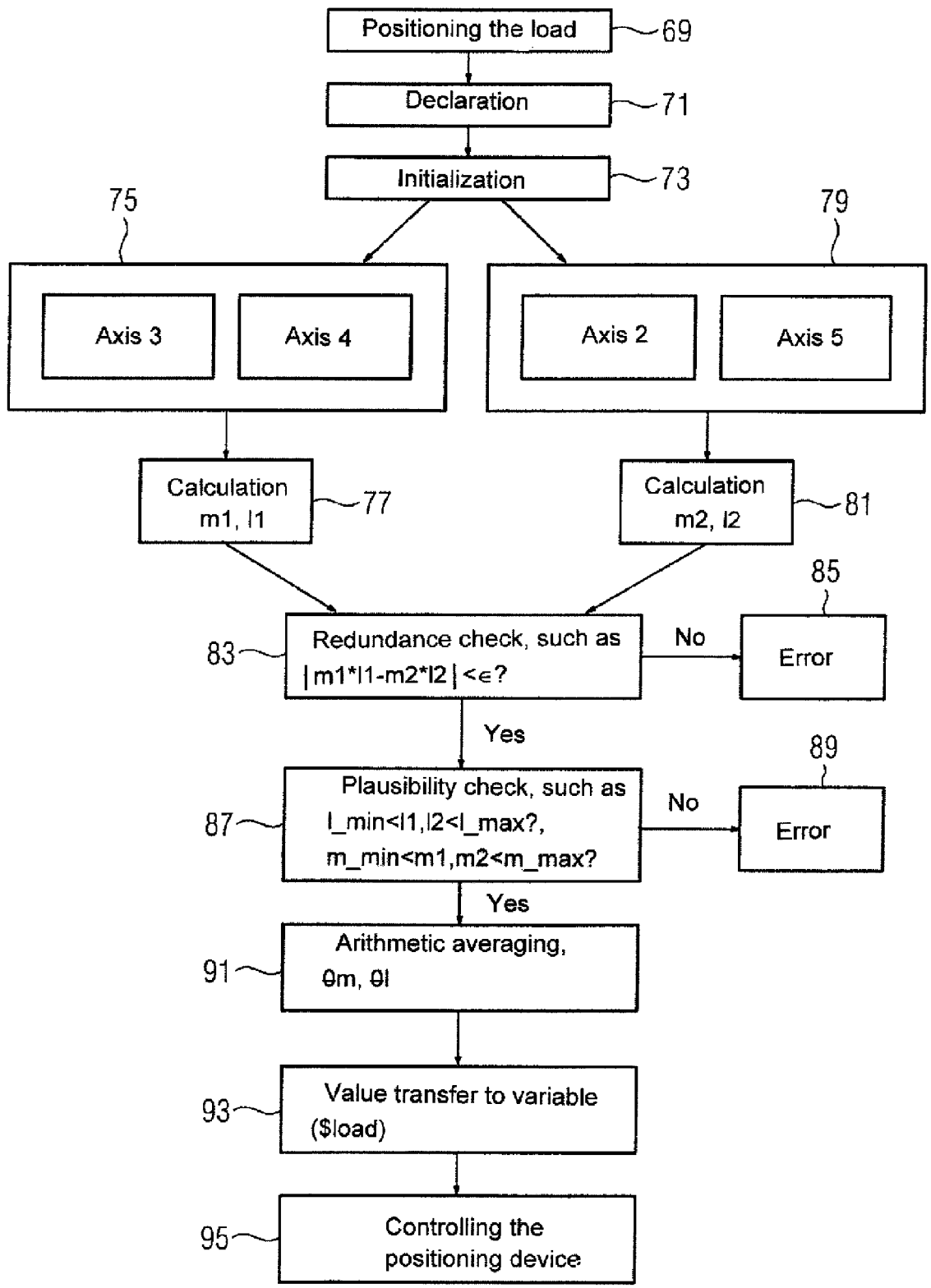

POSITIONING DEVICE AND METHOD FOR POSITIONING A LOAD

This application claims the benefit of DE 10 2007 026 114.6 filed Jun. 5, 2007, which is hereby incorporated by reference.

BACKGROUND

The present embodiments relate to positioning a load.

During particle therapy, a particle beam, for example, including protons or heavy ions, is generated in an accelerator. The particle beam is carried in a radiation channel from the accelerator to an exit window of the radiation channel. The particle beam enters an irradiation or treatment room through the exit window. The particle beam may be used to treat cancer.

The success of tumor treatment depends on the precision of the tumor positioning. Positioning a patient depends on a plurality of factors. For example, the precision of positioning depends on how the patient is supported and the rigidity of the patient support system. In positioning the patient, the weight of the patient may cause elastic deformation that leads to imprecise positioning.

A more-rigid construction may be used to avoid elastic deformation under the load of the patient. However, the more-rigid construction results in higher costs.

Alternatively, it is possible to compensate for elastic deformation, for example, by using known load data to compensate for a predictable deformation. The system cannot be used flexibly, since the load data have to be known prior to treatment. In particle therapy, the load data is not known because of the variability of the loading from one patient to another.

Another possibility is to use sensors, such as force-torque sensors, to ascertain the loading. However, such systems are comparatively expensive.

SUMMARY AND DESCRIPTION

The present embodiments may obviate one or more of the drawbacks or limitations inherent in the related art. For example, in one embodiment, a load is ascertained simply, flexibly, and economically.

In one embodiment, a positioning device for positioning a load includes a motor, measuring device, and an evaluation device. The motor moves the positioning device. The measuring device is associated with the motor and is operable to ascertain (determine) measurement data that characterizes the motor current consumption by the motor in the positioning of the load. The evaluation device may evaluate the measurement data, so that the loading of the positioning device by the load may be ascertained.

The motor current consumption, the force, and/or the torque that act on the motor may be ascertained. Using the geometry of the positioning device, the loading of the positioning device by the load may be attained, for example, without additional sensors. The load data of the load, such as the weight and/or the location of the load on the positioning device, may be ascertained at least in part with the positioning device. The load data of the load does not need to be known prior to treatment.

Based on the ascertained loading of the positioning device, an elastic deformation, for instance, may be quantitatively predicted from the loading. The elastic deformation may be predicated, for example, via a relationship based on empirical values and/or a relationship ascertained by calculation. The deviation in an actual position of the load from a desired set-point position may be ascertained. In static positioning of the load, for example, a warning signal may be output if the ascertained loading is above a threshold value, or if the expected elastic deformation exceeds a tolerance range.

In one embodiment, the positioning device further includes at least one further motor for moving the positioning device; and a further measuring device. The further measuring device is associated with the further motor and is operable to ascertain further measurement data that characterizes the motor current consumption by the further motor in the positioning of the load.

The evaluation device may take into account the further measurement data, in addition to the measurement data, during the evaluation. Because the motor current consumption of further motors is measured, the loading of the positioning device may be ascertained more precisely. For example, loading, or load data, may be ascertained redundantly. The loading may be ascertained more precisely, because variables whose ascertainment requires the measurement data of at least two different motors may be ascertained.

In one embodiment, the positioning device additionally has a control device for positioning the positioning device. The control device may use the ascertained loading to compensate for a deformation.

As a result, it is possible in particular upon static positioning of the load at a desired set-point position to reach the set-point position automatically, even if a deformation of the positioning device by the load occurs. Once the loading is ascertained, the elastic deformation of the positioning device can be determined from it. To that end, a relationship based for instance on experience and/or on calculation can be used. Next, a compensation signal can be ascertained, with which the control device corrects the position of the positioning device accordingly, so that the desired set-point position is reached.

In one embodiment, the evaluation device is operable to ascertain the weight of the load and/or the position of the center of gravity of the load. For example, the position of the load, relative to the positioning device, may be ascertained.

In one embodiment, the positioning device is a multiaxial robot arm with a plurality of joints. The load may be flexibly positioned. By measuring the motor current consumption of at least one motor, which is used to move one of the joints, the loading of the positioning device (e.g., a robot arm) may be ascertained. A deformation of the positioning device by the load may be compensated for.

During the evaluation of the measured measurement data, at least one joint position may be taken into account. At least one joint position may be taken into account whenever the robot arm used in the positioning includes different joint positions for one of the joints. The geometry of the robot arm may be ascertained using the joint position. The geometry of the robot arm may be used to ascertain the center of gravity of the load or the weight of the load. However, if the robot arm for positioning the load has similar joint positions that differ only slightly from one another, then the at least one joint position may not be considered when ascertaining the load, since the geometry of the robot arm varies only insignificantly.

The positioning device may be a patient positioning device for positioning a patient in a medical system, such as in a particle therapy system. This offers a solution to the problem of positioning a patient as precisely as possible in the medical system, and may increase the safety of the system.

In one embodiment, a method for operating a positioning device for positioning a load includes positioning the load by moving the positioning device with the aid of the at least one motor; ascertaining (determining) measurement data that characterize a motor current consumption by the at least one motor in the positioning of the load; evaluating the ascertained measurement data in such a way that loading of the positioning device by the load is ascertained. The method may further include controlling the positioning device using the ascertained loading of the positioning device in such a way that a deformation of the positioning device by the load is compensated for.

The method can be implemented, for example, based on software in a computer unit that is connected to the positioning device for controlling the positioning device. In ascertaining the loading, the weight of the load and/or the position of the center of gravity of the load may, for example be determined as load data.

The ascertained loading of the positioning device may be subjected to a plausibility check, and may increase the reliability of the method.

In one embodiment, the loading in a positioning device, such as a multiaxial robot arm having a plurality of joints may be ascertained. At least one joint position may be taken into account.

In one embodiment, if the positioning device has a plurality of motors, and measurement data is ascertained for each of the motors, the measurement data characterizing the respective motor current consumption in the positioning of the load, then the loading of the positioning device by the load may be ascertained redundantly. For example, an error signal may be output if in the redundant ascertainment a deviation is found that is outside a tolerance range. An error signal may indicate a malfunction of the positioning device, so that motion of the positioning device may be blocked, for example, for safety reasons.

In one embodiment, a medical diagnosis and/or treatment system includes a positioning device for a patient. The positioning device is located in a examination room or treatment room, and the positioning device may include the features discussed above or below. The medical diagnosis and/or treatment system may be used for radiation therapy, such as particle therapy.

BRIEF DESCRIPTION OF THE DRAWINGS

FIG. 3 illustrates a flow chart for a method for ascertaining the loading of a patient positioning device.

DETAILED DESCRIPTION

Figure 1:
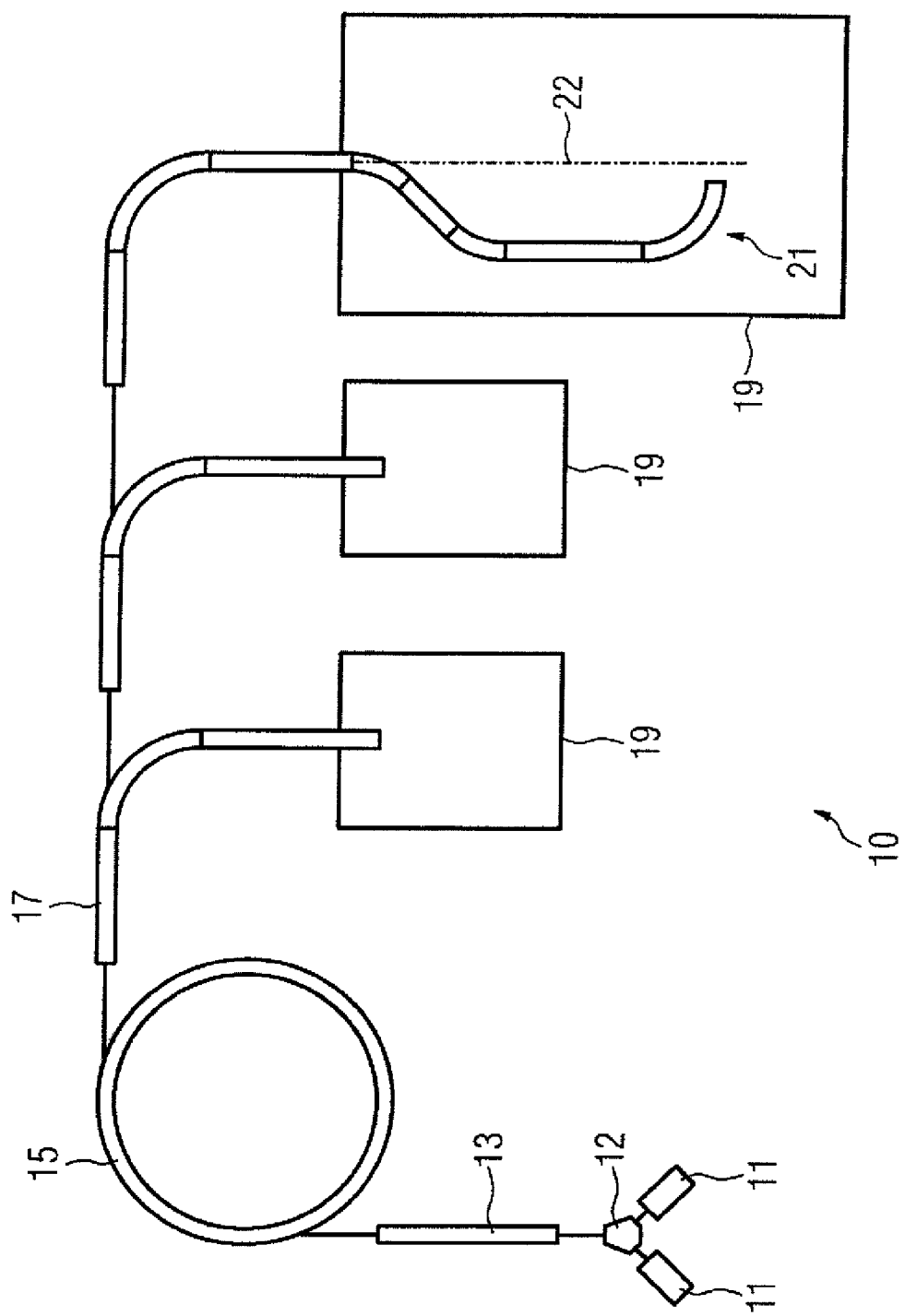
FIG. 1 illustrates one embodiment of a particle therapy system.

FIG. 1 shows a particle therapy system 10. The particle therapy system 10 may be used to irradiate a body, such as tissue diseased by tumor, with a particle beam.

The particles may be ions, protons, pions, helium ions, carbon ions, or other types of ions. The particles may be generated in a particle source 11. If, as shown in FIG. 1, there are two particle sources 11, which generate different types of particles, then a fast switchover between these two types of particles is possible. A switching magnet 12 may be, for example, used for the fast switchover. The switching magnet 12 is located between the particle sources 11 and a preaccelerator 13. For example, the particle therapy system 10 may, for example, be operated with protons and with carbon ions simultaneously.

The ions generated by the ion source or one of the particle sources 11, and optionally selected with the switching magnet 12, are accelerated to a first energy level in the preaccelerator 13. The preaccelerator 13 is, for example, a linear accelerator (LINAC for "LINear ACcelerator"). The particles are fed into an accelerator 15, such as a synchrotron or cyclotron. In the accelerator 15, the particles are accelerated to radiation treatment energies. Once the particles leave the accelerator 15, a high-energy beam transport system 17 carries the particle beam to one or more treatment rooms 19. In the treatment room 19, the accelerated particles are aimed at a body to be irradiated. The accelerated particles may be aimed at a body either from a fixed direction (e.g., in a "fixed beam" room) or from various directions via a movable gantry 21 that is rotatable about an axis 22 (e.g., in a "gantry-based" room).

Figure 2:
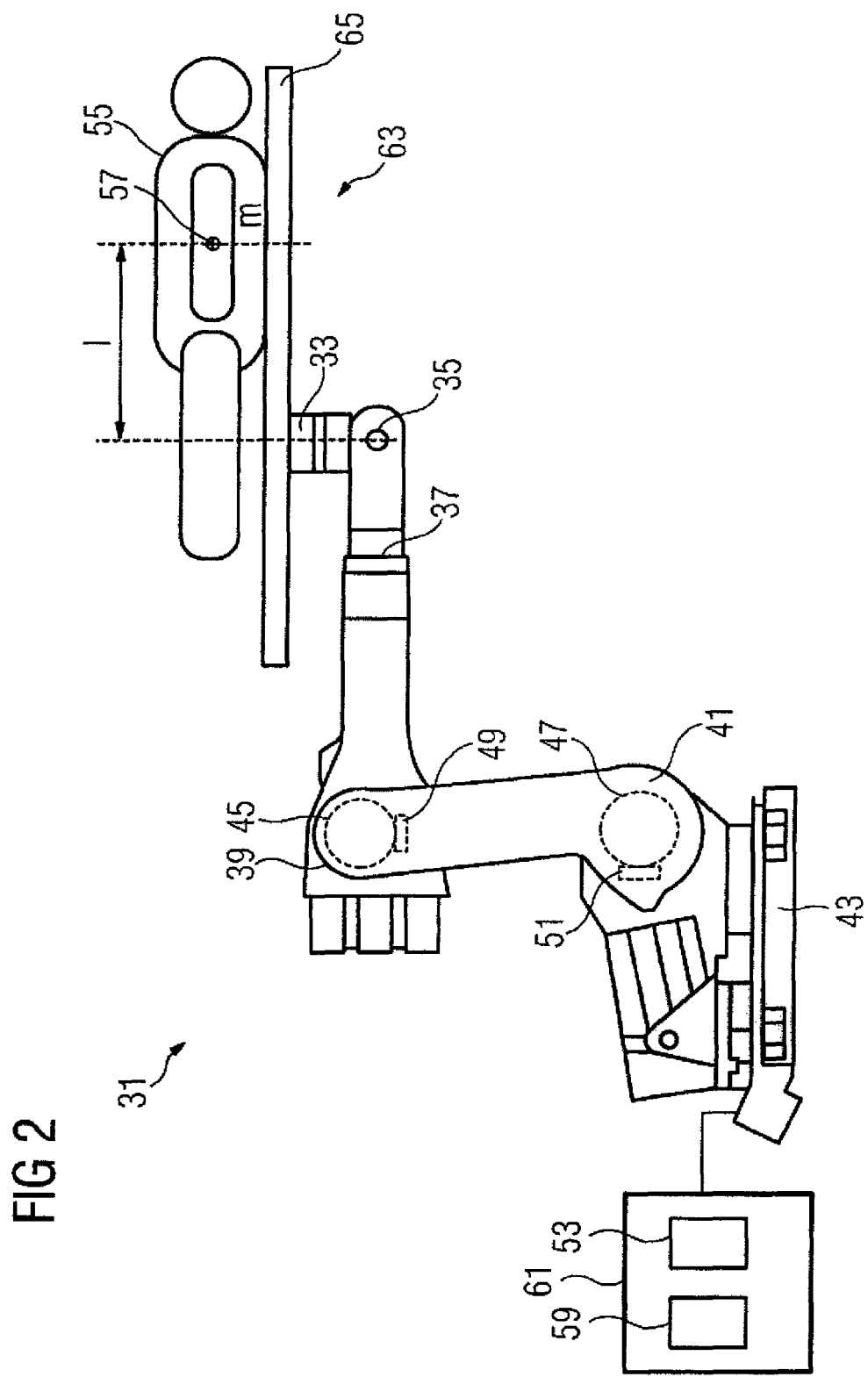
FIG. 2 illustrates one embodiment of a positioning device for a patient.

FIG. 2 shows a positioning device as a robot arm 31. The robot arm 31, for a patient 55, may be used in a treatment room of a particle therapy system.

The robot arm 31 has six different joints 33, 35, 37, 39, 41, 43, which are moved by a motor 45, 47. The motors 45, 47 are located behind the linings of the robot arm 31. Measuring devices 49, 51 are located on (connected to) each of the motors 45, 47, and with them, measurement data that characterizes the motor current consumption at the respective motor 45, 47 upon positioning a patient may be ascertained. The motors 45, 47 and the associated measuring devices 49, 51 are shown at only two joints 39, 41, for the sake of simplicity. A measuring device 49, 51 associated with one of the motors 45, 47 does not need to be located in the immediate vicinity of a motor, as shown. For example, the measuring device 49, 51 may be located in a control unit for the motors 45, 47.

The measurement data is carried to an evaluation device 53. The evaluation device 53 may ascertain the load data for the positioning device. The load data for the positioning device may include the weight m of the patient 55 and the location l of the center of gravity 57 of the patient 55. The load data may be used for oppositely controlling the joints 33, 35, 37, 39, 41, 43 of the robot arm 31 in such a way to compensate for the deformation caused by loading of the positioning device. Compensation may be done, for example, by the control device 59, with which a compensatory motion of the robot 31 may be executed.

The evaluation device 53 and the control device 59 may be implemented, for example, in a computer unit 61 that is connected to the robot arm 31.

The control device 59 may compensate for sagging of the components of the table system 63. Sagging may include, for example, sagging of the tabletop 65, sagging of the table pedestal, or sagging of the tabletop and of the accessories affixed to it.

FIG. 3 shows a flow chart of an embodiment of a method for ascertaining load of a positioning device 31, for example, as shown in FIG. 2.

Proportionality exists between the motor current consumption $I_n$ for a joint n and the torque $M_n$ acting on the joint. The torque $M_n$ is the result of the geometry of the robot arm (position of the individual joints 33, 35, 37, 39, 41, 43) and of the location of the center of gravity of the patient ("l") and the weight of the patient ("m"). The location l and weight m may be unknown variables. Since the geometry (e.g., the position of the individual joints 33, 35, 37, 39, 41, 43) is known, and the motor current consumption may be ascertained with the measuring devices 49, 51, the loading of the positioning device by a patient may be ascertained during the positioning 69.

After declaration 71 and initialization 73 of the variables for ascertaining the loading, a first measurement 75 of the motor current consumption is made at two different joints. Using the first measurement 75, a first calculation 77 of the weight of the patient m1 and of the location of the center of gravity 11 of the patient may be performed.

Similar to this first measurement 75 and first calculation 77, a second measurement 79 of the motor current consumption is made at two further, different joints. Analogously to the first calculation 77, the weight of the patient m2 and the location of the center of gravity 12 of the patient may be calculated in a second calculation 81.

After this twofold, redundant calculation, a redundancy check 83 may be performed. If the variables calculated in the first calculation 77 and in the second calculation 81 differ too greatly, for example, if the difference between the associated torques is greater than a predetermined threshold value $\epsilon$, this is an indication of a malfunction of the system. A first error signal 85 may be output.

The variables calculated may be subjected to a plausibility check 87. The plausibility check 87 may generate a second error signal 89 whenever one of the two calculated values is outside a predetermined tolerance range. The error signal may indicate a malfunction of the system.

If the redundancy check 83 and the plausibility check 87 have not reported any errors, then an arithmetic averaging 91 of the weight m1, m2, calculated twice, of the patient and of the center of gravity 11, 12 of the patient, calculated twice, may be performed.

The averaged variables may be transferred as variables to a computer unit (value transfer 93). These variables may, for example, be used to perform a control 95 of the positioning system, in such a way that compensation for an elastic deformation of the positioning system in positioning the patient is performed.

In one embodiment, a quality check of the positioning system in the context of a quality assurance act, for example, is performed daily. During the quality check, the positioning system is loaded with a defined load, such as with load data known in advance. The method is performed, and the values transferred to the variables may be compared with reference values. When the transferred values are outside a predetermined tolerance range, a malfunction of the positioning device may have occurred.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A positioning system for positioning a mass, the positioning system comprising:
 a robotic arm operable to support the mass, wherein the robotic arm comprises a table system;
 a motor operable to move the robotic arm;
 a measuring device that is associated with the motor and is configured to determine measurement data representing a motor current consumption by the motor in the positioning of the mass; and
 an evaluation device in communication with the measuring device, the evaluation device configured to calculate a location of the mass along the table system of the robotic arm as a function of the measurement data so as to determine a loading of the robotic arm.

2. The positioning system as defined by claim 1, further comprising:
 at least one further motor for moving the robotic arm; and
 a further measuring device that is associated with the at least one further motor and operable to ascertain further measurement data that characterizes a further motor current consumption by the at least one further motor in the positioning of the mass,
 wherein the evaluation device is operable to take the further measurement data into account.

3. The positioning system as defined by claim 1, wherein the robotic arm includes: a control device that positions the robotic arm such that a deformation of the robotic arm by the mass is compensated for using the determined loading.

4. The positioning system as defined by claim 1, wherein the evaluation device is operable to ascertain the weight of the mass, the position of the center of gravity of the mass, or the weight of the mass and the position of the center of gravity of the mass.

5. The positioning system as defined by claim 1, wherein the robotic arm is a multiaxial robot arm.

6. The positioning system as defined by claim 5, wherein the evaluation device is operable to take into account at least one joint position during the determination of the loading as a function of the measurement data.

7. The positioning system as defined by claim 1, wherein the robotic arm is a patient positioning device for positioning a patient in a medical system.

8. The positioning device as defined by claim 7, wherein the medical system is a particle therapy system.

9. The positioning system as defined by claim 1, wherein the robotic arm comprises a multiaxial robot arm with a plurality of joints, and
 wherein the motor is disposed at one joint of the plurality of joints.

10. A method for positioning a mass, the method comprising:
 positioning the mass by moving a robotic arm with at least one motor, wherein the robotic arm comprises a table system;
 determining measurement data that representing a motor current consumption by the at least one motor in the positioning of the mass;
 determining, based on the determined measurement data, a load of the robotic arm, the determining of the load of the robotic arm comprising calculating a location of the mass along the table system of the robotic arm.

11. The method as defined by claim 10, further comprising:
 controlling the robotic arm using the determined load of the robotic arm to compensate for a deformation of the robotic arm by the mass.

12. The method as defined by claim 10, further comprising:
 performing a plausibility check of the determined load.

13. The method as defined by claim 10, wherein
 determining the load includes the weight of the mass, the position of the center of gravity of the mass, or the weight of the mass and the position of the center of gravity of the mass.

14. The method as defined by claim 10, wherein the robotic arm is a multiaxial robot arm with a plurality of joints.

15. The method as defined by claim 14, wherein the determining of the load includes taking into account at least one joint position.

16. The method as defined by claim 10, wherein the at least one motor comprises a plurality of motors,
 wherein in each motor of the plurality of motors, measurement data that characterize the respective motor current consumption in the positioning of the mass are ascertained, and wherein determining the load of the robotic arm by the mass is effected redundantly by evaluating the measurement data ascertained.

17. The method as defined by claim 16, further comprising: outputting an error signal when a deviation between the determined load and a redundant ascertained load that is outside a tolerance range is determined.

18. A medical diagnosis, treatment, or diagnosis and treatment system comprising:
   an examination room or treatment room having a positioning system for a patient, wherein the positioning system comprises:
      a robotic arm operable to support a mass, wherein the robotic arm comprises a table system;
      a motor operable to move the robotic arm;
      a measuring device that is associated with the motor and is configured to determine measurement data representing a motor current consumption by the motor in positioning of the mass; and
      an evaluation device in communication with the measuring device, the evaluation device configured to calculate a location of the mass along the table system of the robotic arm as a function of the measurement data, so that a loading of the robotic arm is determined.

19. The medical diagnosis, treatment, or diagnosis and treatment system as defined by claim 18, further comprising: a radiation therapy device for particle therapy.

20. A particle therapy system comprising:
   a particle source operable to generate particles for irradiating a mass; and
   a positioning system for positioning the mass, the positioning system comprising:
      a robotic arm operable to support the mass, wherein the robotic arm comprises a table system;
      a motor operable to move the robotic arm;
      a measuring device that is associated with the motor and is configured to determine measurement data representing a motor current consumption by the motor in the positioning of the mass; and
      an evaluation device in communication with the measuring device, the evaluation device configured to calculate a location of the mass along the robotic arm as a function of the measurement data so as to determine a loading of the table system of the robotic arm.

* * * * *